United States Patent [19]

De Ridder et al.

[11] 4,244,950
[45] Jan. 13, 1981

[54] DERIVATIVES OF 4-AMINO-3-SULFONAMIDO-PYRIDINE, THEIR PREPARATION AND USE

[75] Inventors: René R. De Ridder, Brussels; André H. Georges, Ottignies; Arlette Ghys, Brussels; Charles L. Lapiere, Tongeren; Jacques E. Delarge, Dolembreux; Léopold N. Thunus, Liege, all of Belgium

[73] Assignee: A. Christiaens Societe Anonyme, Brussels, Belgium

[21] Appl. No.: 6,154

[22] Filed: Jan. 24, 1979

[30] Foreign Application Priority Data

Jan. 31, 1978 [GB] United Kingdom ............... 3918/78

[51] Int. Cl.³ .................. A61K 31/44; A61K 31/445; C07D 213/74; C07D 213/75
[52] U.S. Cl. .................. 424/248.5; 424/250; 424/263; 544/124; 544/130; 544/360; 544/364; 546/187; 546/193; 546/256; 546/261; 546/275; 546/276; 546/278; 546/281; 546/283; 546/306; 546/309
[58] Field of Search ............ 424/263, 248.5, 250; 546/283, 306, 309, 187, 193, 256, 261, 275, 276, 278, 281; 544/124, 130, 360, 364

[56] References Cited

U.S. PATENT DOCUMENTS 3,956,294  5/1976  Eleckenstein et al. .......... 546/309 X Primary Examiner—Richard Raymond
Attorney, Agent, or Firm—Sughrue, Rothwell, Mion, Zinn and Macpeak

[57] ABSTRACT

This invention relates to new derivatives of 4-amino-3-sulfonamido-pyridine having diuretic properties.

The new derivatives of pyridine may be represented by the following general formula:

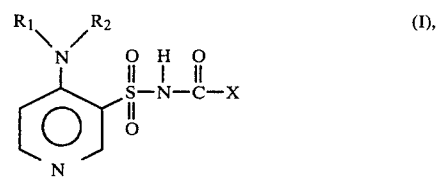

in which
  $R_1$ represents hydrogen or an alkyl, cycloalkyl, carbamoyl or sulfonamido radical;
  $R_2$ represents an alkyl, halogenoalkyl, cycloalkyl, alkenyl, alkynyl, hydroxyalkyl, alkoxyalkyl, phenyl (possibly substituted), phenylalkyl, diphenylmethyl, isobornyl, furfuryl, tetrahydrofurfuryl, dialkylaminoalkyl or heterocyclic radical; or $R_1$ and $R_2$ form together with the nitrogen atom a saturated heterocyclic radical; and
  X represents an alkoxy radical, an heterocyclic amino radical, or a secondary or tertiary amino radical having its first substituent selected from hydrogen and the alkyl and alkenyl groups, and its second substituent selected from the alkyl, alkenyl, alkynyl, hydroxyalkyl, diphenylmethyl, isobornyl, furfuryl, tetrahydrofurfuryl, phenylalkyl and heterocyclic groups.

The invention also relates to salts of addition of said compounds with pharmaceutically acceptable acids.

16 Claims, No Drawings

DERIVATIVES OF 4-AMINO-3-SULFONAMIDO-PYRIDINE, THEIR PREPARATION AND USE

FIELD OF THE INVENTION AND PRIOR ART

This invention relates to derivatives of pyridine having pharmaceutical properties, and more particularly to such derivatives having interesting diuretic activities.

It is presently known, for instance from U.S. Pat. No. 4,018,929, that derivatives of pyridine, such as the 3-lower alkyl carbamyl sulfonamido-4-phenylamino-pyridines may show diuretic properties.

It has now been found surprisingly that certain new derivatives of 4-amino-3-sulfonamido-pyridine have substantially better activities than those observed with the known pyridine compounds. It is therefore an object of this invention to provide new derivatives of pyridine which have interesting diuretic properties.

It is a further object of this invention to provide processes for preparing said new derivatives. A still further object of this invention is to provide for pharmaceutical compositions containing said new derivatives.

BRIEF DESCRIPTION OF THE INVENTION

The new derivates of pyridine are of the following general formula:

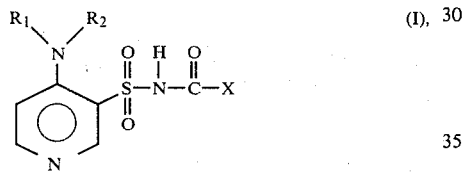 (I), in which $R_1$ represents a hydrogen atom, a straight or branched chain alkyl or cycloalkyl group, a carbamoyl group of the formula

 (II), or a sulfonamido group of the formula

 (III), in which $R_5$ and $R_6$ represent an alkyl radical or form together with the nitrogen atom to which they are attached a saturated heterocyclic radical;

$R_2$ represents a straight or branched chain alkyl group, a halogenoalkyl, cycloalkyl, alkenyl, alkynyl, hydroxyalkyl or alkoxyalkyl group, a possibly substituted phenyl or phenylalkyl radical, a diphenylmethyl, isobornyl, furfuryl or tetrahydrofurfuryl group or a lower dialkylaminoalkyl or a saturated or unsaturated heterocyclic radical; or $R_1$ and $R_2$ from together with the nitrogen atom to which they are bound a possibly substituted saturated nitrogeneous heterocyclic radical; and X represents an alkoxy radical or a group of the formula

 (IV)

in which $R_3$ represents a hydrogen atom, a straighth or branched chain alkyl or an alkenyl group; and $R_4$ represents a straighth or branched chain alkyl radical, an alkenyl, alkynyl or hydroxyalkyl group, a diphenylmethyl, isobornyl, furfuryl, tetrahydrofurfuryl or phenylalkyl group, or a possibly substituted saturated or unsaturated nitrogenous heterocyclic radical possibly containing another heteroatom beside the nitrogen; or $R_3$ and $R_4$ form together with the nitrogen atom to which they are bound, a possibly substituted saturated nitrogenous heterocyclic radical, possibly containing a second heteroatom which may be identical to or different from nitrogen; with the provisos that $R_1$ is different from hydrogen or a $C_1$–$C_4$ alkyl, when $R_2$ represents a possibly substituted phenyl radical or a furfuryl or $C_1$–$C_4$ alkyl group and X represents a

group, in which $R_3$ represents hydrogen and $R_4$ a $C_1$–$C_4$ alkyl or a $C_2$–$C_3$ alkenyl radical, as well as their salts of addition with pharmaceutically acceptable acids.

DETAILED DESCRIPTION OF THE INVENTION

The new compounds according to this invention, i.e. the compounds of formula I, may be prepared by various processes.

First process

When it is desired to obtain a compound of formula (I) wherein $R_1$ and $R_2$ are as generally defined and wherein X represents a

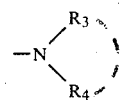

group in which $R_3$ is a hydrogen atom and $R_4$ is as defined above, this process comprises reacting a compound of the following formula

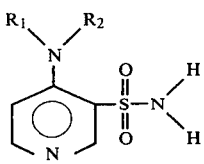 (V), in which $R_1$ and $R_2$ are as defined above, with an isocyanate of the formula $$R_4N=C=O \quad (VI)$$

in which $R_4$ is defined above.

According to a first embodiment of this process the pyridinesulfonamide of formula V is reacted with the isocyanate of formula VI, in the presence of triethylamine.

According to a second embodiment of this first process the pyridinesulfonamide of formula V is used in the form of its sodium salt and reacted directly with isocyanate of formula VI, in the presence of triethylamine.

When it is desired to obtain more particularly a compound of formula VI, wherein $R_1$ is specifically a carbamoyl or a sulfonamido group whereas $R_2$ is as defined, and X represents a

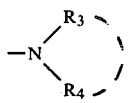

group in which $R_3$ is a hydrogen atom and $R_4$ is as generally defined, one may start from a pyridinesulfonamide of formula V in which $R_1$ represents a hydrogen atom and $R_2$ is as defined, thereby first reacting said compound of formula V with a carbamoyl chloride of formula

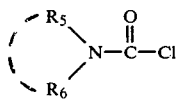 (VII)

or with a sulfonamido chloride of formula

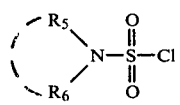 (VIII)

in which $R_5$ and $R_6$ each are as defined above, and thereafter reacting the obtained compound of formula V in which $R_1$ represents a dialkylcarbamoyl or a dialkylsulfamoyl group and $R_2$ is as defined, with an isocyanate of formula VI in which $R_4$ is as defined.

When it is desired to obtain more particularly a compound of formula I wherein $R_1$ is specifically hydrogen and $R_2$ is specifically a saturated nitrogenous heterocyclic radical, whereas X represents a

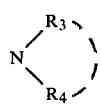

group in which $R_3$ is a hydrogen atom and $R_4$ is as generally defined, one may start from 3-sulfonamidopyridin-4-sulfonic acid of formula

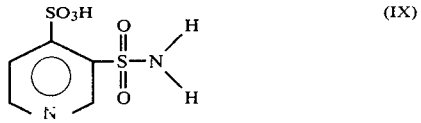 (IX)

thereby first reacting said compound of formula IX, with a N-amino-saturated heterocyclic amine, such as 1-amino-piperidine, and then reacting the obtained compound or formula V in which $R_1$ represents hydrogen and $R_2$ represents a saturated nitrogenous heterocyclic radical, with an isocyanate of formula VI, in which $R_4$ is as defined.

Second process

When it is desired to obtain a compound of formula I wherein $R_1$ and $R_2$ are as generally defined and wherein X represents a

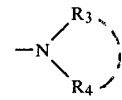

group in which $R_3$ and $R_4$ are as generally defined, this process comprises reacting a compound of the following general formula

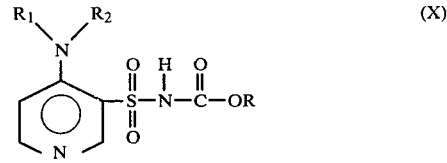 (X)

in which $R_1$ and $R_2$ are as defined above and R represents an alkyl radical, which compound is itself a compound of formula I in which X represents an alkoxy group, with an amine of formula

 (XI)

According to preferred embodiments of this second process of the invention, the pyridine-sulfonylcarbamate of formula X is reacted with an excess of the amine of formula XI in the presence of an organic solvent, such as preferably toluene or chloroform, and 4 Å molecular sieves, either at the reflux temperature of the solvent or at a higher temperature in an autoclave.

Third process

When it is desired to obtain a compound of formula I, wherein $R_1$ is specifically a carbamoyl group or a sulfonamido group, whereas $R_2$ is as generally defined and X represents a

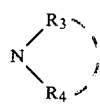

group in which $R_3$ and $R_4$ are as generally defined, this process comprises reacting the sodium salt of a pyridine sufonylurea of formula I, in which $R_1$ is hydrogen and $R_2$, $R_3$ and $R_4$ are as defined, with a carbamoyl chloride of formula VII or with a sulfonamido chloride of formula VIII.

Fourth process

When it is desired to obtain a compound of formula I, wherein $R_1$ is specifically hydrogen, $R_2$ is as generally defined and X represents a

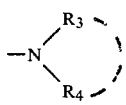

group in which $R_3$ and $R_4$ are as generally defined, this process comprises reacting a 3-oxo-3,4-dihydro-1,2,4-pyrido[4,3-e]-thiadiazin-1,1-dioxide derivative of formula

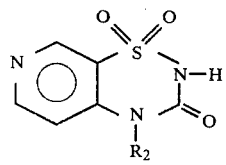

(XII)

in which $R_2$ is as defined, with an excess of amine of formula XI,
in which $R_3$ and $R_4$ are as defined.

This process is preferably carried out in the presence of an organique solvent, such as suitably toluene, at the reflux temperature of the reaction medium.

Fifth process

When it is desired to obtain a compound of formula I wherein $R_1$ and $R_2$ are as generally defined and wherein X represents an alkoxy radical, this process comprises reacting a compound of general formula V in which $R_1$ and $R_2$ are as defined, with an alkyl chloroformate of the following formula

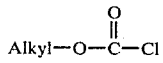

(XIII)

The 4-amino-3-sulfonamido pyridines of formula V which are used as starting materials in the first and fifth processes, may be prepared from 3-sulfonamido-4-chloro-pyridine having the formula

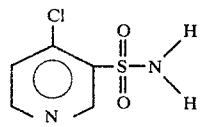

(XIV)

by the following methods:

First method 3-sulfonamido-4-chloropyridine is reacted with an excess of an amine of formula

in which $R_1$ and $R_2$ are as defined above, in the presence of a suitable solvent, such as ethanol, isopropanol or propyleneglycol, at the reflux temperature of the reaction mixture.

This method may also suitably be performed in an autoclave at 140° C., using ethanol as a solvent.

Second method 3-sulfonamido-4-chloropyridine and an excess of an amine of formula XV, in which $R_1$ and $R_2$ are as defined above, are reacted by heating a mixture of both reagents to its melting point.

It has been found that the compounds of formula I have interesting diuretic properties. These properties have been determined by using the following test procedure.

Lots of 3 rats weighting 150–200 g have been selected at random, each lot being submitted to the same treatment. The compound to be tested was administered by gastric gavage at a dose of 50 mg/kg as a solution or a suspension in water containing 0.45% of methylcellulose (which is an inert mucilaginous substance); control animals received only the aqueous vehicle as a placebo.

At the same time, all the animals received physiological saline 25 ml/kg by subcutaneous injection.

The rats were then housed in metabolic cages, each one containing 3 animals being submitted to the same treatment. The urines were collected during a 4 hour period. The increase of urine volume in the treated animals compared with that of the control animals was used to quantify the diuretic action, the diuresis being expressed in ml/kg of body weight. The results of the tests performed in a great number of compounds according to the invention are given in the following table.

TABLE 1

| Pharmacological results | | |
|---|---|---|
| Compound of example n° | Compound of code number | Diuresis ml/kg/4h |
| 41 | C 2947 | 112 |
| 4 | C 2810 | 87 |
| 20 | L 861 | 109 |
| 36 | L 959 | 86 |
| 76 | C 2785 | 86 |
| 77 | C 2862 | 94 |
| 3 | C 2838 | 104 |
| 48 | C 2855 | 95 |
| 27 | L 882 | 89 |
| 10 | C 2744 | 96 |
| 55 | C 2770 | 88 |
| 56 | C 2776 | 87 |
| 5 | L 730 | 98 |
| 26 | L 934 | 85 |
| 68 | C 2963 | 111 |
| 69 | C 2970 | 123 |
| 79 | C 2973 | 128 |
| 71 | C 2721 | 92 |
| 72 | C 2982 | 111 |
| 73 | C 2983 | 111 |
| 39 | L 957 | 87 |
| 22 | L 888 | 98 |

TABLE 1-continued

Pharmacological results

| Compound of example n° | Compound of code number | Diuresis ml/kg/4h |
|---|---|---|
| 38 | L 961 | 86 |
| 31 | L 918 | 89 |

This invention therefore relates also to pharmaceutical compositions containing as active ingredient at least one compound of formula I, or an addition salt thereof with hydrochloric or nitric acid, or with sodium or potassium hydroxide, together with a pharmaceutically acceptable vehicle or carrier.

The compounds of this invention may be administered in the form of dragees, tablets, capsules, suppositories and injections at daily doses of 5 to 50 mg of active compound.

EXAMPLES

The following examples illustrate the preparation of compounds of formula I.

EXAMPLE 1

Preparation of
3-isopropylcarbamoylsulfonamido-4-(3-methylbenzyl)amino-pyridine (formula I: $R_1$=H; $R_2$= 3-methylbenzyl; $R_3$=H; $R_4$=isopropyl). -C 2996-

A. preparation of 3-sulfonamido-4-(3-methylbenzyl)amino-pyridine.

A mixture of 0.01 moles of 3-sulfonamido-4-chloropyridine, 0.02 mole of 3-methylbenzylamine and 50 ml of dry ethanol was heated to reflux temperature for 9 hous. After distillation of the ethanol the residue was taken up in an excess of diluted NaOH and the excess of amine was extracted by means of ether.

The aqueous solution was then decolourized with charcoal and filtered, and the filtrate was neutralized with acetic acid. The precipitated product was separated and purified by crystallization from a mixture of water and acetone.

The product crystallized in the form of beige coloured cristals having a melting point of 184°-186° C.

B. Preparation of 3-isopropylcarbamoylsulfonamido-4-(3-methylbenzyl)amino-pyridine. (first process according to the invention).

0.01 mole of 3-sulfonamido-4-(3-methylbenzyl)amino-pyridine was reacted with 0.015 mole of isopropylisocyanate in the presence of 0.02 mole of triethylamine and of 20 ml of dichloromethane, at room temperature for 20 hours.

After evaporation under vacuum, the residue was taken up in an excess of diluted $Na_2CO_3$, filtered off and acidified by means of acetic acid.

After precipitation of the product it was filtered and washed several times with ice cold water.

The product showing as a white powder, has a melting point of 147°-149° C.

The same reaction was also performed in the absence of a solvent by heating in a hot water bath.

EXAMPLE 2

Preparation of
3-isopropylcarbamoylsulfonamido-4-pentylamino-pyridine nitrate (formula I: $R_1$=H; $R_2$=—$(CH_2)_4$—$CH_3$; $R_3$=H; $R_4$=isopropyl). (First process according to the invention). -L 880-

0.01 mole of the sodium salt of 3-sulfonamido-4-pentylaminopyridine was reacted under stirring with 0.015 mole of isopropylisocyanate, in a mixture of water and acetone in a ratio of 3:2, until disappearance of the pungent isocyanate odour. The hydroacetonic solution or suspension was then treated with an excess of concentrated nitric acid. The precipitate was separated by filtration and washed with ice cold water and recrystallized from water containing a few drops of $HNO_3$. The crystallized product has a melting point of 156°-158° C.

EXAMPLE 3

Preparation of
3-(N-butyl,N-methyl)carbamoylsulfonamido-4-(3-methylphenyl)amino-pyridine (formula I:
$R_1$=hydrogen; $R_2$=3-methylphenyl; $R_3$=methyl; $R_4$=butyl). (Second process according to the invention). C 2838-

0.005 mole of the ethyl carbamate of 3-aminosulfonyl-4-(3-methylphenyl)amino-pyridine was reacted for a few hours with 0.025 mole of N-methyl,N-butylamine, in the presence of 4 Å molecular sieves and of 30 ml of dry toluene; after distillation of the toluene the residue was taken up in an excess of diluted NaOH and the excess of amine was extracted with ether.

The aqueous solution was acidified by means of diluted hydrochloric acid. After its precipitation, the obtained product was purified by means of sodium bicarbonate and reprecipitated by means of the acid.

The obtained product has a melting point of 134°-136° C.

EXAMPLE 4

Preparation of
3-(N-isopropyl,N-benzyl)carbamoyl-sulfonamido-4-(3-methylphenyl)amino-pyridine. (Formula I: $R_1$=H; $R_2$=3-methylphenyl; $R_3$=isopropyl; $R_4$=benzyl). (Second process according to the invention). -C 2810-

A mixture of 0.005 mole of the ethylcarbamate of 3-aminosulfonyl-4-(3-methylphenyl)amino-pyridine, 0.025 mole of isopropylbenzylamine and dry toluene (or dry chloroform) were heated for 20 hours at 100° C. in an autoclave in the presence of 4 Å molecular sieves.

The compound was isolated and purified in the same manner as described in example 3. The precipitated product has a melting point of 140-142.

EXAMPLE 5

Preparation of
3-ethylcarbamoylsulfonamido-4-[N-(3-chlorophenyl),N-(diethylcarbamoyl)]amino-pyridine.
(Formula I: $R_1$=diethylcarbamoyl;
$R_2$=3-chlorophenyl; $R_3$=hydrogen; $R_4$=ethyl). - L 730 -

A. preparation of 3-sulfonamido-4-[N-(3-chlorophenyl),N(diethylcarbamoyl)]amino-pyridine (same method as the third process according to the invention).

0.01 mole of 3-sulfonamido-4-(3-chlorophenyl)amino-pyridine was heated with 0.03 mole of diethylcarbamoylchloride in the presence of 5 ml of trietehylamine, until a thick slurry was obtained, which was maintained in this state for 10 minutes. The slurry was then taken up with 50 ml of an alcohol-water mixture in a ratio 1:3, and frankly alkalinized with ammonia. The product was allowed to crystallize, filtered and washed with diluted ammonia and the with water.

The thus obtained product as purified by crystallization from diluted alcohol; it has a melting moint of 143°–144° C.

B. Preparation of 3-ethylcarbamoylsulfonamido-4-[N-(3-chlorophenyl),N-(diethylcarbamoyl)]amino-pyridine. (First process according to the invention).

3-sulfonamido-4-[N-(3-chlorophenyl),N-(diethylcarbamoyl)]amino-pyridine was reacted with 2 to 3 times the theoretically needed amount of ethylisocyanate, in the presence of an excess of triethylamine, by heating the mixture in a hot water bath.

When the reaction products had completely liquefied, the mixture was taken up in alcohol in order to dissolve it and then added to an excess of water. A few ml of ammonia and absorbing coal were added to the mixture which was stirred for some minutes, and then filtered. The filtrate was neutralized to a pH of 5–6.

The precipitate was recovered and washed with water. It has a melting point of 168°–169° C.

EXAMPLE 6

Preparation of 3-isopropylcarbamoylsulfonamido-4-[N-(3-trifluoromethylphenyl),N-(diethylcarbamoyl)]amino-pyridine (Formula I: $R_1$=diethylcarbamoyl; $R_2$=m.trifluoromethylphenyl; $R_3$=hydrogen; $R_4$=isoprophl) - L 740 -

This compound was prepared by using the method described in example 5, thereby using 3-sulfonamido-4-(3-trifluoromethylphenyl)amino-pyridine instead of 3-sulfonamido-4-(3-chlorophenyl)amino-pyridine and isopropylisocyanate instead of ethylisocyanate.

The obtained purified product has a melting point of 148°–150° C.

EXAMPLE 7

Preparation of 3-isopropylcarbamoylsulfonamido-4-[N-(3-methylphenyl),N-(diethylcarbamoyl)]amino-pyridine. (Formula I: $R_1$=diethylcarbamoyl; $R_2$=3-methylphenyl; $R_3$=hydrogen; $R_4$=isopropyl). (Third process according to the invention). - C 2932 -

0.01 mole of the sodium salt of 3-isopropylcarbamoylsulfonamido-4-(3-methylphenyl)amino-pyridine was reacted for 48 hours at room temperature with 0.01 mole of diethylcarbamoylchloride in dimethylformamide. The reaction mixture was then poured on ice and the thus obtained precipitate was filtered. The product which was purified by cristallization from isopropanol, has a melting point of 175°–158° C.

EXAMPLE 8

Preparation of 3-isopropylcarbamoylsulfonamido-4-[N-(3-methylphenyl),N-(1-piperidinosulfonyl)]amino-pyridine. (Formula I: $R_1$=piperidinosulfonyl; $R_2$=3-methylphenyl; $R_3$=hydrogen; $R_4$=isopropyl). - C 2975 -

This compound was prepared by using the method described in example 7, thereby using 1-piperidinosulfonyl chloride instead of diethylaminocarbamoylchloride. The obtained product has a decomposition point of 108° C.

EXAMPLE 9

Preparation of 3-isopropylcarbamoylsulfonamido-4-(1-piperidino)amino-pyridine (Formula I: $R_1$=hydrogen; $R_2$=1-piperidino; $R_3$=hydrogen; $R_4$=isopropyl). - L 944 -

A. Preparation of 3-sulfonamido-4-(1-piperidino)amino-pyridine.

0.02 mole of 3-sulfonamido-pyridine-4-sulfonic acid was heated for 2 hours with 0.06 mole of 1-aminopiperidine and 6 ml of water, at reflux temperature. The reaction mixture was then diluted and allowed to crystallize upon cooling.

The precipitate was filtered off, washed with water and dried. It has a melting point of 225°–227° C.

B. Preparation of 3-isopropylcarbamoylsulfonamido-4-(1-piperidino)amino-pyridine. (First process according to the invention).

0.01 mole of 3-sulfonamido-4-(1-piperidino)amino-pyridine was heated for 5 hours to reflux temperature by means of a boiling hot water bath with 3 times the theoretical amount of isopropylisocyanate and an excess of triethylamine.

The obtained syrupy liquid was taken up with diluted soda and some alcohol until complete dissolution.

The mixture was then acidified to a pH of 3–4 and the thus obtained precipitate was filtered, washed with a little water and purified by means of sodium bicarbonate and reprecipitation with acid.

The precipitate was filtered off, washed with water and dried. It has a melting point of 240°–241° C.

EXAMPLE 10

Preparation of 3-(N-tetramethylene)carbamoylsulfonamido-4-(3-methylphenyl)amino-pyridine (Formula I: $R_1$=hydrogen; $R_2$=3-methylphenyl; $R_3$ and $R_4$ form together —$CH_2$—$CH_2$—$CH_2$—$CH_2$). -C 2744 -

A. By the fourth process according to the invention:
a mixture of 0.005 mole of 3-oxo-4-(3-methylphenyl)-3,4-dihydro-1,2,4-pyrido[4,3-e]-thiadiazin-1,1-dioxide, 0.025 mole of pyrrolidine and toluene was heated for 45 hours at reflux temperature.

After distillation of the toluene, the residue was taken up in water and the mixture was acidified by means of diluted hydrochloric acid. After its precipitation the obtained product was purified by means of sodium bicarbonate and reprecipitated with acid. The thus obtained product has a melting point of 158°–160° C.

B. By the second process according to the invention:
the same product was also obtained by reacting the ethyl carbamate of 3-aminosulfonyl-4-(3methylphenyl)amino-pyridine with pyrrolidine in the presence of molecular sieves, using the method described in example 3.

EXAMPLE 11

Preparation of 3-(N-furfuryl)carbamoylsulfonamido-4-(3-methylphenyl)amino-pyridine (Formula I: $R_1$=hydrogen; $R_2$=3-methylphenyl; $R_3$=hydrogen; $R_4$=furfuryl). - C 2754 -

A. By the fourth process according to the invention: this compound was prepared by reacting 3-oxo-4-(3-methylphenyl)-3,4-dihydro-1,2,4-pyrido[4,3-e]-thiadiazin-1,1-dioxide with furfurylamine, using thereby the general method described in example 10A.

The obtained product has a melting point of 157°–158° C.

B. By the second process according to the invention: this same compound was also prepared by reacting the ethylcarbamate of 3-aminosulfonyl-4-(3-methylphenyl)amino-pyridine with furfurylamine in the presence of molecular sieves, using the general method described in example 3.

EXAMPLE 12

Preparation of the ethylcarbamate of 3-aminosulfonyl-4-(N-benzyl,N-ethyl)amino-pyridine (Formula I: $R_1$=ethyl; $R_2$=benzyl; X=O $C_2H_5$). - C 2938 -

A. Preparation of 3-sulfonamido-4-(N-benzyl,N-ethyl) amino-pyridine.

A mixture of 0.01 mole of 3-sulfonamido-4-chloropyridine and 0.02 mole of N-ethyl,N-benzylamine was gradually heated to 125° C. during 15 minures. After cooling the residue was taken up in an excess of diluted NaOH; the excess of amine was extracted with ether, the aqueous solution was discoloured with charcoal and filtered. The filtrate was then neutralized with acetic acid. The precipitated product was recovered, and purified by crystallization from benzene. It has a melting point of 150°–152° C.

B. Preparation of the ethyl carbamate of 3-aminosulfonyl-4-(N-benzyl,N-ethyl)amino-pyridine. (Fifth method according to the invention).

0.01 mole of 3-sulfonamido-4-(N-benzyl,N-ethyl)amino-pyridine, in the form of its sodium salt, was reacted for eight hours at room temperature with 0.011 mole of ethyl chloroformate in 20 ml of dry tetrahydrofuran. After distillation of the tetrahydrofuran, the obtained product was purified by crystallization from a mixture of ethanol/water. The purified product has a decomposition point of 199° C.

EXAMPLES 13 TO 23

The following compounds, listed in table II herebelow, were prepared by using the method described in example 1 hereabove.

TABLE II

Compound of formula I: $R_1$ = hydrogen; $X = N\begin{smallmatrix}H\\R_4\end{smallmatrix}$

| Example no. | Compound code no. | $R_2$ | $R_4$ | Melting point (°C.) |
|---|---|---|---|---|
| 13 | C 2995 | $-CH_2-$(4-Cl-phenyl) | $-CH(CH_3)_2$ | 140–142 |
| 14 | C 2864 | $-CH_2-$phenyl | $-CH(CH_3)_2$ | 146–148 |
| 15 | C 2929 | $-CH(C_6H_5)_2$ | $-CH(CH_3)_2$ | 135 |
| 16 | C 2905 | $-CH_2-CH_2-$phenyl | $-CH(CH_3)_2$ | 133–135 |
| 17 | C 2933 | 2-acetyl-phenyl ($COCH_3$) | $-CH(CH_3)_2$ | 100–103 |
| 18 | C 2921 | cyclopropyl(bicyclic) | $-CH(CH_3)_2$ | 168–170 |
| 19 | C 2914 | $-CH_2-$(tetrahydrofuryl-O) | $-CH(CH_3)_2$ | 88–90 |

TABLE II-continued

Compound of formula I:
$R_1$ = hydrogen; $X = N\begin{smallmatrix}H\\ \diagdown\\ R_4\end{smallmatrix}$

| Example no. | Compound code no. | $R_2$ | $R_4$ | Melting point (°C.) |
|---|---|---|---|---|
| 20 | L 861 | cyclohexyl-H | $-CH\begin{smallmatrix}CH_3\\ \diagup\\ \diagdown CH_3\end{smallmatrix}$ | 185–187 |
| 21 | L 886 | $-(CH_2)_6-CH_3$ | $-CH\begin{smallmatrix}CH_3\\ \diagup\\ \diagdown CH_3\end{smallmatrix}$ | 139–141 |
| 22 | L 930 | $-CH_2CH_2CH_2OH$ | $-CH\begin{smallmatrix}CH_3\\ \diagup\\ \diagdown CH_3\end{smallmatrix}$ | 182–184 |
| 23 | L 933 | $-(CH_2)_3-O-CH\begin{smallmatrix}CH_3\\ \diagup\\ \diagdown CH_3\end{smallmatrix}$ | $-CH\begin{smallmatrix}CH_3\\ \diagup\\ \diagdown CH_3\end{smallmatrix}$ | 128–130 |

EXAMPLES 24 TO 39

The following compounds listes in table III herebelow were prepared by using the method described in example 2 hereabove.

TABLE III

Compound of formula I:
$R_1$ = hydrogen; $X = N\begin{smallmatrix}H\\ \diagdown\\ R_4\end{smallmatrix}$

| Example no. | Compound code no. | $R_2$ | $R_4$ | Melting point (°C.) |
|---|---|---|---|---|
| 24 | L 882 | cyclopentyl | $-CH\begin{smallmatrix}CH_3\\ \diagup\\ \diagdown CH_3\end{smallmatrix}$ | 182–184 nitrate |
| 25 | L 884 | $-(CH_2)_5-CH_3$ | $-CH\begin{smallmatrix}CH_3\\ \diagup\\ \diagdown CH_3\end{smallmatrix}$ | 163–165 nitrate |
| 26 | L 890 | $CH_3-CH-CH_2-CH_2-CH\begin{smallmatrix}CH_3\\ \diagup\\ \diagdown CH_3\end{smallmatrix}$ | $-CH\begin{smallmatrix}CH_3\\ \diagup\\ \diagdown CH_3\end{smallmatrix}$ | 156–157 nitrate |
| 27 | L 915 | $-CH\begin{smallmatrix}CH_2\\ \diagup\ \mid\\ \diagdown CH_2\end{smallmatrix}$ | $-CH\begin{smallmatrix}CH_3\\ \diagup\\ \diagdown CH_3\end{smallmatrix}$ | 174–176 nitrate |
| 28 | L 918 | $-CH\begin{smallmatrix}CH_2CH_3\\ \diagup\\ \diagdown CH_2CH_3\end{smallmatrix}$ | $-CH\begin{smallmatrix}CH_3\\ \diagup\\ \diagdown CH_3\end{smallmatrix}$ | 113–115 nitrate |
| 29 | L 931 | $-CH_2-CH_2-O-CH_3$ | $-CH\begin{smallmatrix}CH_3\\ \diagup\\ \diagdown CH_3\end{smallmatrix}$ | 160–162 nitrate |
| 30 | L 932 | $-(CH_2)_3-O-C_2H_5$ | $-CH\begin{smallmatrix}CH_3\\ \diagup\\ \diagdown CH_3\end{smallmatrix}$ | 153–155 nitrate |
| 31 | L 936 | $-CH_2-CH=CH_2$ | $-CH\begin{smallmatrix}CH_3\\ \diagup\\ \diagdown CH_3\end{smallmatrix}$ | 158–160 nitrate |

TABLE III-continued

Compound of formula I:
$R_1$ = hydrogen; X = N(H)(R_4)

| Example no. | Compound code no. | $R_2$ | $R_4$ | Melting point (°C.) |
|---|---|---|---|---|
| 32 | L 941 | 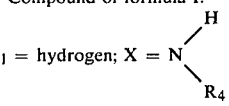 (cyclooctyl) | —CH(CH$_3$)$_2$ | 161–162 nitrate |
| 33 | L 959 | 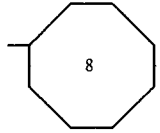 (cyclohexyl-H) | —CH$_2$—CH$_3$ | 180–182 nitrate |
| 34 | L 960 | 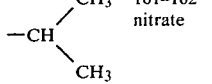 (cyclopentyl) | —CH$_2$—CH$_3$ | 186–188 nitrate |
| 35 | L 961 | 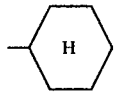 (cyclooctyl) | —CH$_2$—CH$_3$ | 155–157 nitrate |
| 36 | L 957 | —CH$_2$—C≡CH | —CH(CH$_3$)$_2$ | 160–161 nitrate |
| 37 | L 888 | 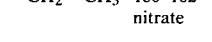 (cycloheptyl) | —CH(CH$_3$)$_2$ | 163–165 nitrate |
| 38 | L 919 | —(CH$_2$)$_3$—N(CH$_3$)$_2$ | —CH(CH$_3$)$_2$ | 110–112 nitrate |
| 39 | L 934 | —CH$_2$CH$_2$CH$_2$Cl | —CH(CH$_3$)$_2$ | 161–163 |

EXAMPLES 40 TO 75

The following compounds, listed in table IV herebelow were prepared by using the method described in example 3 hereabove.

TABLE IV

Compound of formula I
X = N(R_3)(R_4) (ring)

| Example no. | Compound code no. | | | | Melting point (°C.) |
|---|---|---|---|---|---|
| 40 | C 2927 | $R_1$ = H | $R_2$ = —C$_4$H$_9$ | 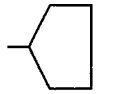 | 170–172 |
| 41 | C 2947 | $R_1$ = H | $R_2$ = 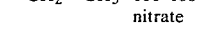 (cyclohexyl) | 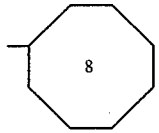 | 166–169 |
| 42 | C 2930 | $R_1$ = C$_2$H$_5$ | $R_2$ = —C$_4$H$_9$ | 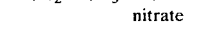 | 187–189 |

TABLE IV-continued

Compound of formula I $$X = N\begin{matrix}R_3\\R_4\end{matrix}$$

| Example no. | Compound code no. | | | | Melting point (°C.) |
|---|---|---|---|---|---|
| 43 | C 2974 | $R_1 = C_6H_{11}$ | $R_2 = CH_2-CH=CH_2$ | $N\begin{matrix}R_3\\R_4\end{matrix} = -N\bigcirc O$ (morpholino) | 195–197 |
| 44 | C 2925 | $R_1 = C_4H_9$ | $R_2 = C_4H_9$ | $N\begin{matrix}R_3\\R_4\end{matrix} = -N\bigcirc O$ (morpholino) | 208–210 |
| 45 | C 2939 | $R_1 = H$ | $R_2 = CH_3-CH(-C_6H_5)-CH_2$ | $N\begin{matrix}R_3\\R_4\end{matrix} = -N\bigcirc O$ (morpholino) | 196–198 |
| 46 | C 2942 | $R_1 = C_2H_5$ | $R_2 = -CH_2-C_6H_5$ | $N\begin{matrix}R_3\\R_4\end{matrix} = -N$ (piperidino) | 148–150 |
| 47 | C 3008 | $N\begin{matrix}R_1\\R_2\end{matrix} = -N$ (2-methylpiperidino) | | $N\begin{matrix}R_3\\R_4\end{matrix} = -N$ (piperidino) | 181–183 |
| 48 | C 2855 | $R_1 = H$ | $R_2 = $ 3-methylphenyl | $R_3 = C_2H_5$, $R_4 = C_4H_9$ | 133–135 |
| 49 | C 2836 | $R_1 = H$ | $R_2 = $ 3-methylphenyl | $R_3 = C_2H_5$, $R_4 = CH_2-CH_2OH$ | 137–139 |
| 50 | C 2825 | $R_1 = H$ | $R_2 = $ 3-methylphenyl | $R_3 = H$, $R_4 = -CH(C_2H_5)_2$ | 125–127 |
| 51 | C 2795 | $R_1 = H$ | $R_2 = $ 3-methylphenyl | $R_3 = H$, $R_4 = -CH(C_6H_5)_2$ | 193–194 |
| 52 | C 2773 | $R_1 = H$ | $R_2 = $ 3-methylphenyl | $R_3 = -CH_2-CH=CH_2$, $R_4 = -CH_2-CH=CH_2$ | 138–140 |
| 53 | C 2788 | $R_1 = H$ | $R_2 = $ 3-methylphenyl | $R_3 = H$, $R_4 = -CH_2-C\equiv CH$ | 175–176 |
| 54 | C 2834 | $R_1 = H$ | $R_2 = $ 3-methylphenyl | $R_3 = CH_3$, $R_4 = -CH_2-C_6H_5$ | 158–160 |

TABLE IV-continued

Compound of formula I $$X = N\begin{smallmatrix}R_3 \\ R_4\end{smallmatrix}$$

| Example no. | Compound code no. | | | | Melting point (°C.) |
|---|---|---|---|---|---|
| 55 | C 2770 | $R_1 = H$, $R_2 = $ 3-methylphenyl | | $N\begin{smallmatrix}R_3\\R_4\end{smallmatrix} = -N\bigcirc O$ (morpholino) | 149-151 |
| 56 | C 2776 | $R_1 = H$, $R_2 = $ 3-methylphenyl | | $= -N$ (piperidino) | 155-158 |
| 57 | C 2777 | $R_1 = H$, $R_2 = $ 3-methylphenyl | | $= -N$ (hexamethyleneimino) | 123-125 |
| 58 | C 2782 | $R_1 = H$, $R_2 = $ 3-methylphenyl | $R_3 = H$ | $R_4 = -N\bigcirc O$ | 141-143 |
| 59 | C 2784 | $R_1 = H$, $R_2 = $ 3-methylphenyl | | $= -N\bigcirc N-CH_3$ | 161-163 |
| 60 | C 2774 | $R_1 = H$, $R_2 = $ 3-methylphenyl | $R_3 = H$ | $R_4 = $ 2-piperidyl | 163-165 |
| 61 | C 2791 | $R_1 = H$, $R_2 = $ 3-methylphenyl | $R_3 = H$ | $R_4 = -N$ (piperidino) | 120-122 |
| 62 | C 2796 | $R_1 = H$, $R_2 = $ 3-methylphenyl | $R_3 = H$ | $R_4 = $ N-ethylpiperidyl | 176-178 |
| 63 | C 2867 | $R_1 = H$, $R_2 = $ 3-methylphenyl | $R_3 = C_2H_5$ | $R_4 = -CH_2-C_6H_5$ | 156-158 |
| 64 | C 2843 | $R_1 = H$, $R_2 = $ 3-methylphenyl | | $= -N\bigcirc O$ (2,6-dimethylmorpholino) | 162-164 |
| 65 | C 2857 | $R_1 = H$, $R_2 = $ 3-methylphenyl | $R_3 = H$ | $R_4 = $ norbornyl | 165-168 |

TABLE IV-continued

Compound of formula I $$X = N\begin{smallmatrix}R_3\\R_4\end{smallmatrix}$$

| Example no. | Compound code no. | | | | Melting point (°C.) |
|---|---|---|---|---|---|
| 66 | C 2833 | $R_1 = H$ | $R_2 =$ 3-methylphenyl | $N\begin{smallmatrix}R_3\\R_4\end{smallmatrix} = -N\text{(piperazinyl)}N-CH_3$ | 181 dihydrochloride. |
| 67 | C 2979 | $R_1 = H$ | $R_2 =$ 3-methylphenyl | $N\begin{smallmatrix}R_3\\R_4\end{smallmatrix} = -N\text{(3-methylpiperidyl)}$ | 129–131 |
| 68 | C 2963 | $R_1 = H$ | $R_2 =$ 3-chlorophenyl | $N\begin{smallmatrix}R_3\\R_4\end{smallmatrix} = -N\text{(morpholinyl)}$ | 165–167 |
| 69 | C 2970 | $R_1 = H$ | $R_2 =$ 3-chlorophenyl | $N\begin{smallmatrix}R_3\\R_4\end{smallmatrix} = -N\text{(pyrrolidinyl)}$ | 150–152 |
| 70 | C 2732 | $R_1 = H$ | $R_2 =$ 3-trifluoromethylphenyl | $N\begin{smallmatrix}R_3\\R_4\end{smallmatrix} = -N\text{(pyrrolidinyl)}$ | 160–162 |
| 71 | C 2721 | $R_1 = H$ | $R_2 =$ 3-trifluoromethylphenyl | $N\begin{smallmatrix}R_3\\R_4\end{smallmatrix} = -N\text{(piperidyl)}$ | 142–144 |
| 72 | C 2982 | $R_1 = H$ | $R_2 =$ 3-methylphenyl | $N\begin{smallmatrix}R_3\\R_4\end{smallmatrix} = -N\text{(3,5-dimethylpiperidyl)}$ | 158–159 |
| 73 | C 2983 | $R_1 = H$ | $R_2 =$ 3-methylphenyl | $N\begin{smallmatrix}R_3\\R_4\end{smallmatrix} = -N\text{(4-phenylpiperidyl)}$ | 130–132 |
| 74 | C 2998 | $R_1 = CH_3$ | $R_2 = -CH_2-C\equiv CH$ | $N\begin{smallmatrix}R_3\\R_4\end{smallmatrix} = -N\text{(piperidyl)}$ | 184–186 |
| 75 | C 2999 | $R_1 = H$ | $R_2 =$ 3-methylphenyl | $N\begin{smallmatrix}R_3\\R_4\end{smallmatrix} = -N\text{(piperazinyl)}N\text{-(chlorophenyl)}$ | 148–151 |

EXAMPLES 76 TO 83

The following compounds listed in table V herebelow were prepared by using the method described in example 4 hereabove.

TABLE V

Compound of formula I:

$$X=N\begin{subarray}{c}R_3\\ \\R_4\end{subarray}$$

| Example no. | Compound code no. | R₁ | R₂ | R₃ | R₄ | Melting point (°C.) |
|---|---|---|---|---|---|---|
| 76 | C 2785 | H | 2-methylphenyl (CH₃) | CH₃ | CH₃ | 165–166 |
| 77 | C 2862 | H | 2-methylphenyl (CH₃) | C₂H₅ | C₂H₅ | 144–146 |
| 78 | C 2869 | H | 2-methylphenyl (CH₃) | C₄H₉ | C₄H₉ | 131–133 |
| 79 | C 2973 | H | 2-chlorophenyl (Cl) | C₂H₅ | C₂H₅ | 141–143 |
| 80 | C 2896 | H | 2-(trifluoromethyl)phenyl (CF₃) | C₄H₉ | C₄H₉ | 124–126 |
| 81 | C 2942 | C₂H₅ | —CH₂—phenyl | $N(R_3)(R_4)$ = piperidino | | 148–150 |
| 82 | C 2863 | H | 2-methylphenyl (CH₃) | H | —CH₂—(tetrahydrofuran-2-yl) | 162–163 |
| 83 | C 2850 | H | 2-methylphenyl (CH₃) | $N(R_3)(R_4)$ = 4-methylpiperidino | | 149–151 |

EXAMPLES 84 TO 94

The following compounds listed in table VI herebelow were prepared by using the method described in example 12 hereabove.

TABLE VI

| Example no. | Compound code no. | Compound of formula I: X = OC₂H₅ | | Melting point (°C.) |
|---|---|---|---|---|
| | | R₁ | R₂ | |
| 84 | C 2919 | H | C₄H₉ | 143–145 |
| 85 | C 2924 | H | cyclohexyl | 184–185 |
| 86 | C 2926 | C₂H₅ | C₄H₉ | 204–206 |
| 87 | C 2967 | C₆H₁₁ | CH₂—CH=CH₂ | 186–188 |
| 88 | C 2920 | C₄H₉ | C₄H₉ | 194–196 |

TABLE VI-continued

| Example no. | Compound code no. | Compound of formula I: X = OC$_2$H$_5$ | | Melting point (°C.) |
|---|---|---|---|---|
| | | R$_1$ | R$_2$ | |
| 89 | C 2934 | H | CH$_3$—CH—CH$_2$—〇 | 153 (dec) |
| 90 | C 2941 | 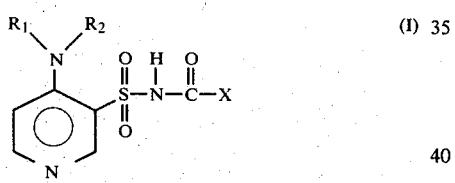 | | 184–186 |
| 91 | C 2667 | H | CH$_3$ on phenyl | 148–150 |
| 92 | C 2960 | H | Cl on phenyl | 155–157 |
| 93 | C 2673 | H | CF$_3$ on phenyl | 147–149 |
| 94 | C 2953 | CH$_3$ | CH$_2$—C≡CH | 204–206 |

We claim:

1. A compound of the following general formula

  (I)

in which

R$_1$ represents a hydrogen atom, a straight or branched chain alkyl group, a cycloalkyl group, a carbamoyl group of the formula

  (II)

or a sulfonamide group of the formula (III)

in which R$_5$ and R$_6$ represent an alkyl group or together complete a hydrocarbon chain, forming with the nitrogen atom to which they are bound, a saturated nitrogen-containing heterocyclic ring;

R$_2$ represents a straight or branched chain alkyl group, a haloalkyl group, a cycloalkyl group, an alkenyl group, an alkynyl group, a hydroxyalkyl group, an alkoxyalkyl group, a phenyl group, a phenylalkyl group, a diphenylmethyl group, an isobornyl group, a furfuryl group, a tetrahydrofurfuryl group, a lower dialkylaminoalkyl group or a saturated or unsaturated nitrogen-containing heterocyclic ring; or R$_1$ and R$_2$ complete together a hydrocarbon chain, forming, with the nitrogen atom to which they are bound, a saturated nitrogen-containing heterocyclic ring, which may be unsubstituted or substituted with one or more alkyl groups, and X represents an alkoxy group or a group of the formula

  (IV)

in which

R$_3$ represents a hydrogen atom, a straight or branched chain alkyl group, or an alkenyl group; and R$_4$ represents a straight or branched chain alkyl group, an alkenyl group, an alkynyl group, a hydroxyalkyl group, a diphenylmethyl group, an isobornyl group, a furfuryl group, a tetrahydrofurfuryl group, a phenylalkyl group, a pyridyl group or a saturated nitrogen-containing heterocyclic ring;

or R$_3$ and R$_4$ complete together, with the nitrogen atom to which they are bound, a saturated nitrogen-containing heterocyclic ring, a saturated dinitrogen-containing diheterocyclic ring or a saturated nitrogen- and oxygen-containing diheterocyclic ring;

with the provisos that $R_1$ is different from a hydrogen atom or a $C_1$–$C_4$ alkyl group, when $R_2$ represents a phenyl group, a furfuryl group or a $C_1$–$C_4$ alkyl group, and X represents a

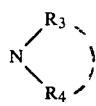

group, in which $R_3$ represents a hydrogen atom and $R_4$ represents a $C_1$–$C_4$ alkyl group or a $C_2$–$C_3$ alkenyl group, as well as the pharmaceutically acceptable acid and basic addition salts.

2. A compound according to claim 1, in which $R_1$ represents a hydrogen atom and $R_2$ represents a phenyl group, X being different from a $C_1$–$C_4$ alkylamino group or a $C_2$–$C_3$ alkenylamino group.

3. A compound according to claim 1, in which $R_1$ represents a hydrogen atom and $R_2$ represents an alkyl group, a cycloalkyl group, a haloalkyl group, a hydroxyalkyl group, an alkenyl group, an alkynyl group, or a lower dialkylamino group.

4. A compound according to claim 1, in which $R_1$ represents a dialkylcarbamoyl group of the formula (II) and $R_2$ represents a phenyl group.

5. A compound according to claim 1, 2, 3, or 4, in which X represents a dialkylamino group or a nitrogen-containing heterocyclic ring.

6. A compound according to claim 3, or 4, in which X represents an alkylamino group.

7. A compound according to claim 1, in which $R_2$ is an unsubstituted phenyl group or an unsubstituted phenylalkyl group.

8. A compound according to claim 1, in which $R_4$ is an unsubstituted saturated nitrogen-containing heterocyclic ring.

9. A compound according to claim 1, in which $R_3$ and $R_4$ complete, together with the nitrogen atom to which they are bound, an unsubstituted saturated nitrogen-containing heterocyclic ring, an unsubstituted saturated dinitrogen-containing diheterocyclic ring or an unsubstituted saturated nitrogen- and oxygen-containing diheterocyclic ring.

10. A compound according to claim 1, in which $R_2$ is a phenyl group or a phenylalkyl group in which the phenyl moiety thereof is halo substituted, methyl substituted, trifluoromethyl substituted or acetyl substituted.

11. A compound according to claim 1, in which $R_4$ is a saturated nitrogen-containing heterocyclic ring substituted with an alkyl group.

12. A compound according to claim 1, in which $R_3$ and $R_4$ complete, together with the nitrogen atom to which they are bound, a saturated nitrogen-containing heterocyclic ring, a saturated dinitrogen-containing diheterocyclic ring, or a saturated nitrogen- and oxygen-containing diheterocyclic ring, wherein said rings are substituted by an alkyl group, a phenyl group or a halophenyl group.

13. A compound according to claim 2, in which $R_2$ is an unsubstituted phenyl group.

14. A compound according to claim 4, in which $R_2$ is an unsubstituted phenyl group.

15. Compounds according to claim 1, wherein said compound of the general formula (I) is

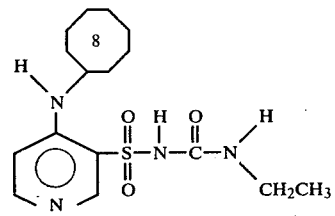

16. A pharmaceutical composition containing as an active ingredient at least one compound of the formula (I), as defined in claim 1, or a pharmaceutically acceptable acid or basic addition salt thereof together with a pharmaceutically acceptable vehicle or carrier.

* * * * *